US009587254B2

(12) United States Patent
Jo et al.

(10) Patent No.: US 9,587,254 B2
(45) Date of Patent: Mar. 7, 2017

(54) METHOD FOR PRODUCING USEFUL SUBSTANCE FROM CELLULOSE-CONTAINING MATERIAL

(75) Inventors: Sung-Jin Jo, Nagoya (JP); Risa Nakamura, Toyota (JP); Satoshi Katahira, Nagoya (JP); Nobuhiro Ishida, Seto (JP); Haruo Takahashi, Ogaki (JP); Naoko Takahashi, legal representative, Ogaki (JP); Kazuhide Tabata, Toyota (JP); Kazunori Nakashima, Kobe (JP); Chiaki Ogino, Kobe (JP); Akihiko Kondo, Kobe (JP)

(73) Assignees: KABUSHIKI KAISHA TOYOTA CHUO KENKYUSHO, Aichi (JP); TOYOTA JIDOSHA KABUSHIKI KAISHA, Toyota (JP)

( * ) Notice: Subject to any disclaimer, the term of this patent is extended or adjusted under 35 U.S.C. 154(b) by 724 days.

(21) Appl. No.: 12/850,966

(22) Filed: Aug. 5, 2010

(65) Prior Publication Data

US 2011/0033906 A1 Feb. 10, 2011

(30) Foreign Application Priority Data

Aug. 6, 2009 (JP) .................................. 2009-183880

(51) Int. Cl.
*C12P 7/10* (2006.01)
(52) U.S. Cl.
CPC ............. *C12P 7/10* (2013.01); *C12P 2201/00* (2013.01); *Y02E 50/16* (2013.01); *Y02E 50/17* (2013.01)
(58) Field of Classification Search
None
See application file for complete search history.

(56) References Cited

U.S. PATENT DOCUMENTS

| 6,808,557 | B2 | 10/2004 | Holbrey et al. |
| 6,824,599 | B2 | 11/2004 | Swatloski et al. |
| 2008/0227162 | A1 | 9/2008 | Varanasi et al. |
| 2010/0279372 | A1* | 11/2010 | Cho et al. ........... 435/165 |

FOREIGN PATENT DOCUMENTS

| JP | A-2005-506401 | 3/2005 |
| JP | A-2006-137677 | 6/2006 |
| JP | A-2008-86310 | 4/2008 |

OTHER PUBLICATIONS

Dadi et al. (Biotechnol. & Bioengin., vol. 95, No. 5, Dec. 5, 2006).*
Singhania et al. (Enzyme & Microb. Tech., vol. 46, 2010, pp. 541-549).*
Kamiya et al. (Biotech. Lett., 2008, vol. 30, pp. 1037-1040).*
Whitfield et al. (Indust. Crops & Products, vol. 37, 2012, pp. 362-375).*
Spindler et al. ( Human Press Inc., 1988, 279-293).*
Fadeev et al. (Chem. Commun., 2001, pp. 295-296).*
Kadar et al. (Indust. Crops & Prod., vol. 20, 2004, pp. 103-110).*
Kuo et al. (Biores. Tech., vol. 100, 2009, pp. 866-871).*
Li et al. (Biores. Tech., vol. 100, 2009, pp. 3570-3575).*
Nguyen et al. (Int'l J. of Hydrogen Energy, vol. 33, 2008, pp. 5161-5168).*
Tan et al. (Green Chemistry. vol. 11, 2009, pp. 339-345).*
Lee et al. (Adv. Biochem. Engin/Biotech., vol. 87, 2004, pp. 173-194).*
Li et al. (Bioresource Tech., vol. 100, Mar. 28, 2009, pp. 3570-3575).*
Kadar et al. ( Science Direct, Industrial Corps. & Products, vol. 20, 2004, pp. 103-110).*
Saha et al. (Process Biochem., vo. 40, pp. 3693-3700).*
Zheng et al. (Biotechnol. Prog., 1998, vol. 14, No. 6, 1998).*
Kamiya et al. (Biotechnol. Letters, vol. 30, pp. 1037-1040, 2008).*
Swatloski, R.P. et al., "Dissolution of Cellulose with Ionic Liquids," *Journal of the American Chemical Society*, 2002, pp. 4974-4975, vol. 124, No. 18, published by the American Chemical Society, USA.
Sekikawa, K. et al., "Cellulase-catalyzed Hydrolysis of Cellulose in Ionic Liquids," *Polymer Preprints*, 2006, p. 2090, vol. 55, No. 1, Japan (with Abstract).
Fukaya, Y. et al, "Polar Ionic Liquids: Required Factors of Anions for Dissolution of Polysaccharides," *Polymer Preprints*, 2007, pp. 2198-2199, vol. 56, No. 1, Japan (with Abstract).
Turner , M.B. et al., "Ionic Liquid Salt-Induced Inactivation and Unfolding of Cellulase From *Trichoderma reesei,*" *Green Chemistry*, 2003, pp. 443-447, vol. 5, published by the Royal Society of Chemistry.
Dadi, A.P. et al., "Enhancement of Cellulose Saccharification Kinetics Using an Ionic Liquid Pretreatment Step," *Biotechnology and Bioengineering*, Dec. 5, 2006, pp. 904-910, vol. 95, No. 5, published by Wiley Periodicals, Inc.
Li, Q. et al., "Improving Enzymatic Hydrolysis of Wheat Straw Using Ionic Liquid 1-ethyl-3-methyl Imidazolium Diethyl Phosphate Pretreatment," *Bioresource Technology*, 2009, pp. 3570-3575, vol. 100, published by Elsevier Ltd.
Collection of Abstracts, Annual Meeting of the Japan Society for Bioscience, Biotechnology and Agrochemistry, pp. 43, 2008.
Collection of Research Presentation Abstracts, Annual Meeting of the Japan Wood Research Society, pp. 15-1315, Feb. 2009.
Commemorative Symposium on Enzyme Engineering, Japan Society of Enzyme Engineering, pp. 88, May 2009.

(Continued)

*Primary Examiner* — Hope Robinson
(74) *Attorney, Agent, or Firm* — Oliff PLC

(57) ABSTRACT

The present invention provides a method for producing a useful substance efficiently from cellulose without using any cellulase preparation. According to the disclosures of the present specification, in the production of a useful substance from a cellulose-containing material, the cellulose-containing material is brought into contact with an ionic liquid to cause the ionic liquid to permeate the cellulose-containing material, and a carbon source comprising the cellulose in the cellulose-containing material is simultaneously saccharified and fermented by a cellulase-producing microorganism in the presence of the ionic liquid.

17 Claims, 10 Drawing Sheets

(56) References Cited

OTHER PUBLICATIONS

Matsumoto et al., "Toxicity of Ionic Liquids and Organic Solvents to Lactic Acid-Producing Bacteria", Journal of Bioscience and Bioengineering, pp. 344-347, 2004, vol. 98, No. 5.
Japanese Office Action dated Jan. 17, 2012 issued in Japanese Patent Application No. 2009-183800 (with translation).

\* cited by examiner

| 0 h | 24 h | 48 h | 72 h | 96 h | 120 h | 144 h | 168 h |

Immersion in ionic liquind and treatment at 120°C for 1hour    Collection of ionic liquid    Fermentation after adding buffur, recombinant yeast and medium    Arming yeast

METHOD FOR PRODUCING USEFUL SUBSTANCE FROM CELLULOSE-CONTAINING MATERIAL

CROSS-REFERENCE TO RELATED APPLICATION(S)

This application claims priority to Japanese Patent Application No. 2009-183880 filed on Aug. 6, 2009, the contents of which are hereby incorporated by reference into the present application.

Technical Field

The present invention relates to a method for producing a useful substance from a cellulose-containing material.

Description of Related Art

Biomass, which is derived from plant photosynthesis, is increasingly being seen as a replacement for limited petroleum resources. Various attempts have therefore been made to apply biomass to energy and various materials. The importance of biorefineries as a means of using biomass and applying it to chemical products and bio fuels is also being recognized, and technologies are being developed for practical application. In order for biomass to be used effectively as an energy source or raw material, it must be broken down and saccharified into carbon sources that can easily be utilized by animals and microorganisms. One issue that needs to be resolved for practical application is the development of efficient method for decomposing the cellulose, and particularly, the crystalline cellulose, that is the primary component of woody and herbaceous biomass.

In existing saccharification processes, the biomass is pretreated by high temperature/high pressure treatment or acid treatment to decompose the cellulose before cellulase is applied. However, the pretreatment presents a serious problem for practical application because it uses a great deal of energy and requires a large quantity of cellulase.

Recently, it has been reported that ionic liquid solubilizes cellulose. For example, the property of solubilizing cellulose under a condition of about 100° C. has been found in a chloride ionic liquid (Patent Document 1, Non-patent Document 1). A non-chloride ionic liquid has also been found to solubilize cellulose under a milder condition (Patent Document 2, Non-patent Documents 2, 3, 4).

Other efforts involve using cellulase to saccharify cellulose that has been solubilized with ionic liquid, but it has been reported that cellulase is inactivated in ionic liquid (Non-patent Documents 2, 4). It has been reported that after cellulose has been pretreated by being solubilized with ionic liquid, the solubilized cellulose can be washed with water or another hydrophilic solvent to remove the ionic liquid, and then placed in water and broken down with cellulase (Non-patent Document 5).

Another method that has been tried is to swell the cellulose with ionic liquid, remove the ionic liquid, and then subject the cellulose to enzyme treatment (Patent Document 3, Non-patent Document 6).

1. Japanese Translation of PCT Application PCT/US2002/031404 (JP Publication No. 2005-506401)
2. Japanese Patent Application Publication No. 2006-137677
3. U.S. Patent Application Publication US 2008/0227162 A1

1 Swatloski et al., J. Am. Chem. Soc. 124(18), 4974-4975, 2002
2. Sekikawa et al., Polym. Prep. Jpn. 55(1), 2090, 2006
3. Fukaya et al., Polym. Prep. Jpn., 56(1), 2198-2199, 2007
4. Turner et al., Green Chem. 5, 443-447, 2003
5. Dadi et al., Biotechnol. Bioeng., 95(5), 904-910, 2006
6. Q. Li et al., Bioresour. Technol., Vol. 100, p 3570-3575, 2009

SUMMARY

However, all of the above technologies focus on saccharification from cellulose, using commercial cellulase preparations for the saccharification reactions in all cases and the saccharified product as the fermentation feedstock. That is, in the production of useful substances from actual biomass and other cellulose-containing materials, the pretreatment, saccharification and fermentation of the cellulose-containing material have each been studied separately. Reasons for this include the fact that lignocellulose normally requires harsh pretreatment conditions because of its tough composite structure, and the fact that cellulase preparations have been convenient for efficiently decomposing cellulose.

However, cellulase is one cause of increased costs in the production of alcohol and other useful substances from biomass. Moreover, as disclosed in the aforementioned prior art, even if a cellulose-containing material is pretreated with an ionic liquid, no method is yet known by which the cellulose-containing material, after being treated with the ionic liquid, can be saccharified and useful substances efficiently produced with microorganisms.

It is an object of the present invention to provide a method for producing useful substances efficiently from cellulose with avoiding or reducing a cellulase preparation.

The inventors investigated the resistance of microorganisms to ionic liquids with the idea that the poor efficiency and difficulty of conventional pretreatment, saccharification and fermentation might be improved upon by applying microorganisms directly to the cellulose-containing material after treatment with an ionic liquid. As a result, it has been discovered for the first time that yeasts and other microorganisms are capable of surviving ionic liquids at certain concentrations, and of simultaneously saccharifying and fermenting cellulose. The disclosures of the present specification are provided based on these findings.

The disclosures of the present specification provide a method for producing a useful substance from a cellulose-containing material, including the following steps (a) and (b):

(a) a step of bringing a cellulose-containing material into contact with an ionic liquid to cause the ionic liquid to permeate the cellulose-containing material;

(b) a step of using a cellulase-producing microorganism to simultaneously saccharify and ferment a carbon source comprising the cellulose in the cellulose-containing material in the presence of the ionic liquid.

In this production method, the step (a) may further comprise heating the cellulose-containing material and the ionic liquid. This production method may also be provided with the following step (c) after the step (a):

(c) a step of performing solid-liquid separation for separating a cellulose-containing fraction from a non-cellulose-containing fraction.

In this case, the following step (d) may further be provided:

(d) a step of collecting the ionic liquid that is the non-cellulose-containing fraction separated in the step (e), and supplying the ionic liquid to the step (a).

The ionic liquid may further comprise hydrophilic ionic liquid. The step (b) may also be a step of using a cellulase-expressing recombinant yeast as the microorganism, and the microorganism may be a yeast that secretes or surface-displays cellulase.

DETAILED DESCRIPTION OF INVENTION

The disclosures of the present specification provide a method for producing a useful substance from a cellulose-containing material. According to the disclosures of the present specification, a cellulose-containing material is first brought into contact with an ionic liquid, and saccharification and fermentation are performed simultaneously with a cellulase-producing microorganism using a carbon source comprising the cellulose-containing material in the presence of the ionic liquid. The inventors in this case have discovered for this first time that even in the presence of ionic liquid, a microorganism that produces cellulase (referred to as a "cellulase-producing microorganism" hereinbelow) has the property of being able to survive and simultaneously saccharify and ferment cellulose has been decomposed, disintegrated or structurally relaxed by means of ionic liquid. Before submission of this application, ionic liquid was considered to have harmful effects or toxicity with respect to cellulase and microorganisms, and in order to avoid these ill effects, saccharification was performed only after the ionic liquid had been removed by thorough washing of the cellulose-containing material following ionic liquid treatment in the aforementioned prior art.

By using this property of cellulase-producing microorganisms with respect to ionic liquids as discovered by the inventors, it is possible to produce a useful substance by simultaneous saccharification and fermentation of a cellulose-containing material in which the cellulose has been decomposed, disintegrated or structurally relaxed with an ionic liquid. As a result, harsh and energy-intensive pretreatment steps and saccharification steps using cellulase and other enzyme preparations are avoided, and useful substances can be simply and efficiently produced from cellulose-containing materials.

Figure 1:
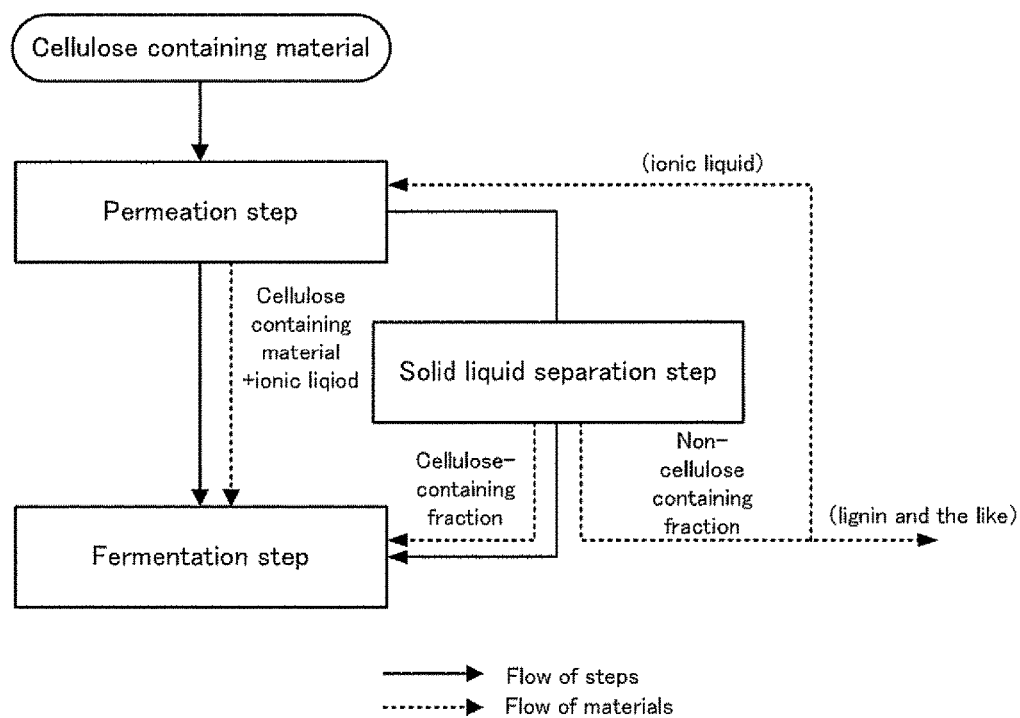
FIG. 1 shows one example of the flow of the method for producing a useful substance disclosed in the present specification.
Figure 2:
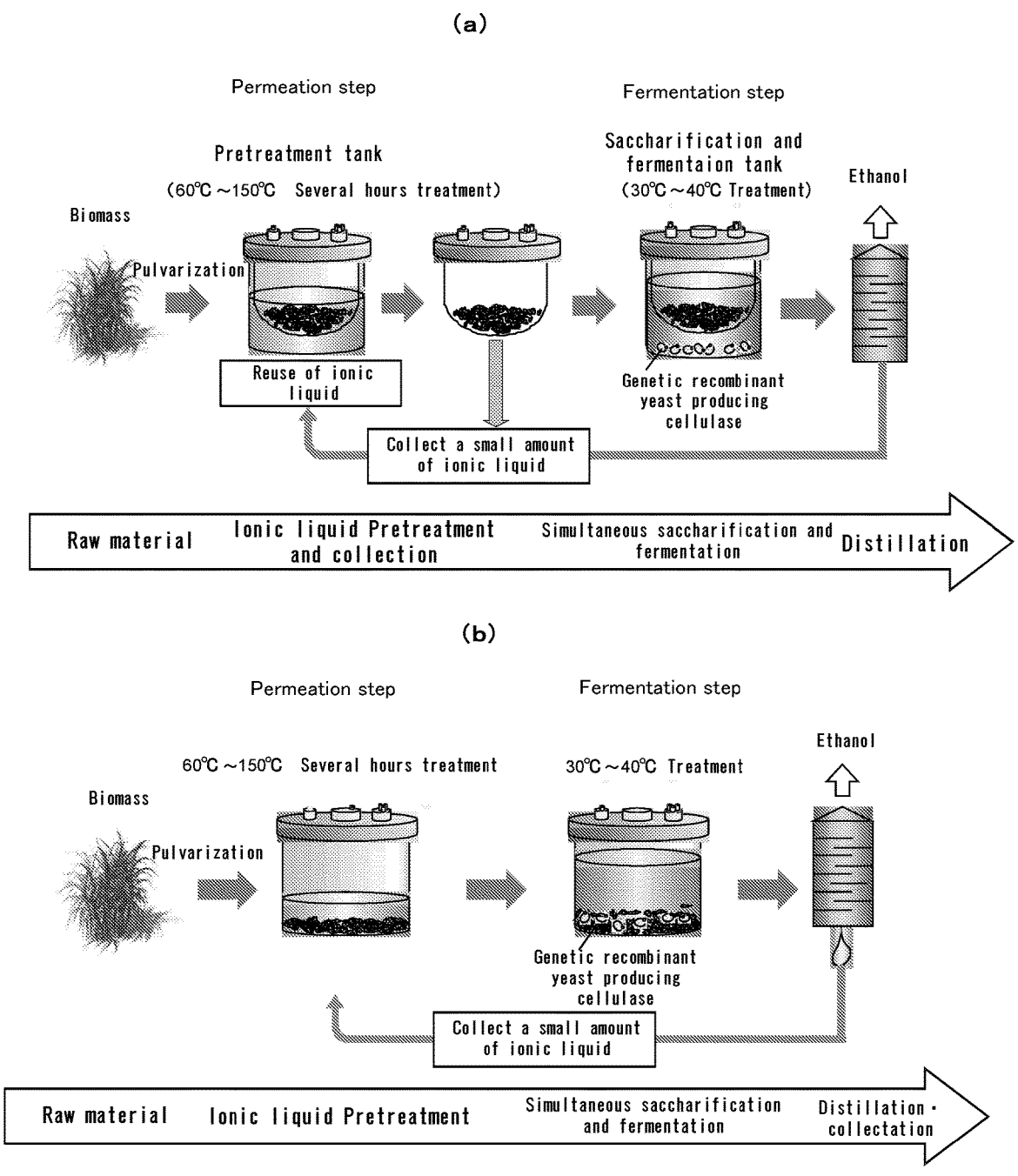
FIG. 2 shows an embodiment of the method for producing a useful substance disclosed in the present specification.

The various embodiments disclosed in the present specification are explained in detail below with reference to the appropriate drawings. FIG. 1 shows one example of the flow of the method for producing a useful substance disclosed in the present specification, while FIG. 2 shows a typical example of the method for producing a useful substance disclosed in the present specification.

(Method for Producing Useful Substance from Cellulose-Containing Material)
(Cellulose-Containing Material)

In the present specification, "cellulose" refers to polymers and derivatives of polymers formed from glucose by polymerization with $\beta$-1,4-glucoside bonds. The degree of polymerization of the glucose in the cellulose is not particularly limited but is preferably 200 or more. Examples of derivatives include those that have been carboxymethylated, aldehyde modified or esterified or the like. The cellulose may further include its partial decomposition products, cellooligosaccharides and cellobiose. The cellulose may also be lignocellulose (a composite of cellulose with beta-glucoside, lignin and/or hemicellulose glycosides), or a composite with pectin or the like. The cellulose may be crystalline cellulose or amorphous cellulose, but preferably includes crystalline cellulose. The cellulose may be naturally derived or artificially synthesized. The origin of the cellulose is not particularly limited, and it may be derived from plants, fungi or bacteria.

In the present specification, the cellulose-containing material may be any that contains the aforementioned cellulose. The cellulose may be crystalline cellulose or amorphous cellulose, and hemicellulose or lignin may further be included in addition to cellulose. Examples of cellulose-containing materials include cotton, hemp and other natural fibers, rayon, cupra, acetate, Lyocell and other reclaimed fibers, rice straw and other kinds of straw, rice chaff, bagasse, wood chips and other agricultural waste products, used paper, construction waste and other waste products, and other kinds of woody and herbaceous biomass.

There are no particular limits on the cellulose-containing materials that can be applied to the production method disclosed in the present specification. As disclosed in the examples below, ionic liquids are known to partially dissolve, disintegrate or structurally relax cellulose even if it is crystalline or forms a matrix with lignin. That is, even if highly crystalline regions are formed in the cellulose by strong interactions due to hydrogen bonding as in crystalline cellulose, the ionic liquid can permeate and dissolve, disintegrate or structurally relax the cellulose, thereby promoting disintegration by cellulase. Considering the effects of ionic liquids on matrices containing cellulose as discovered by the inventors in this case, moreover, the cellulose-containing material is preferably one that is insoluble or slightly soluble in water. The cellulose-containing material may be a cellulose-containing material that contains crystalline cellulose, or a material comprising a cellulose-containing matrix derived from plant cell walls that contain lignin and/or hemicellulose in addition to cellulose. Typically, it is herbaceous or woody biomass.

When the cellulose-containing material is actual biomass having lignocellulose or the like, it is preferably pulverized or otherwise refined as needed prior to the permeation step in order to enhance permeability by the ionic liquid and improve saccharification efficiency. It may also be refined during the permeation step.

(Useful Substance)

The useful substance is not particularly limited, and may be any that can be produced by a microorganism using glucose. Examples include ethanol, propanol, isopropanol, butanol, isobutanol and other lower alcohols, fine chemicals produced by addition of isoprenoid biosynthesis pathways (coenzyme Q10, vitamins and vitamin raw materials and the like), lactic acid and other organic acids, glycerin, plastics, chemical synthesis materials and the like produced by glycolytic modification, and other raw materials for biorefinery technology.

(Permeation Step)

The method for treating a cellulose-containing material disclosed in the present specification may include a step of bringing the cellulose-containing material into contact with an ionic liquid to thereby cause the ionic liquid to permeate the cellulose-containing material. In the permeation step, the ionic liquid, which is a liquid phase, is brought into contact with the cellulose-containing material, which is a solid phase. The ionic liquid has permeability with respect to the cellulose-containing matrix of the cellulose-containing material, and the ability to dissolve, disintegrate or structurally relax at least part of the cellulose-containing material. In many cases, the cellulose is a polymer material having both hydrophobic and hydrophilic regions, although this is not a limitation on the disclosures of the present specification. The affinity of the ionic liquid for water differs depending on the combination of cations and anions therein, and because the cellulose has both hydrophobic and hydrophilic regions as discussed above, it is assumed that the liquid can permeate the cellulose-containing matrix and relax the structure of the cellulose in a variety of ways. It is also assumed that in addition to its permeability with respect to cellulose, the ionic liquid also has permeability with respect to the lignin and hemicellulose that are present together with cellulose in actual biomass, and also has the effect of interacting with these and relaxing their structures. By whatever means, it appears to assist the action of the cellulase by at least relaxing the structure of the cellulose, and perhaps also relaxing the structures surrounding the cellulose.

(Ionic Liquid)

Various ionic liquids can be used in the permeation step. Because a liquid state is required for the fermentation step, the melting point of the liquid is preferably 80° C. or less, and more preferably 40° C. or less, or still more preferably 20° C. or less. The type of ionic liquid used in the permeation step is not limited, and hydrophobic ionic liquids and hydrophilic ionic liquids can be used. In light of the subsequent fermentation step, it is desirable to use a hydrophilic ionic liquid. In the present specification, a hydrophilic ionic liquid is an ionic liquid that mixes with water without biphasic separation. A hydrophilic ionic liquid may be at least an ionic liquid that mixes with water within the temperature range of fermentation by the microorganism. A hydrophilic ionic liquid having permeability with respect to cellulose-containing material is e.g. an ionic liquid capable of suspending or dispersing the cellulose-containing material when mixed with it.

The hydrophilic ionic liquid is not particularly limited, but examples include quaternary ammonium salts, quaternary phosphonium salts, substituted imidazolium salts substituted with hydrocarbon groups and the like, substituted pyridinium salts, substituted piperidinium salts (cyclic quaternary ammonium salts), tertiary sulfonium salts and the like, and quaternary ammonium salts, quaternary phosphonium salts, substituted imidazolium salts, substituted pyridinium salts and substituted piperidinium salts can be used by preference for the ionic liquid in the present invention. Quaternary ammonium salts, quaternary phosphonium salts, substituted imidazolium salts, substituted pyridinium salts and substituted piperidinium salts are represented by General Formulae (I) through (V) below, respectively.

[C1]

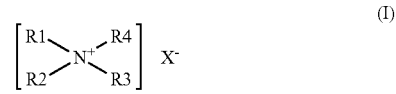
(I)

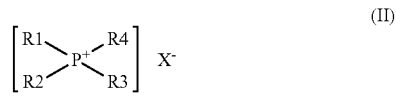
(II)

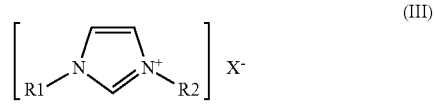
(III)

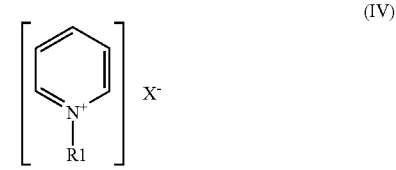
(IV)

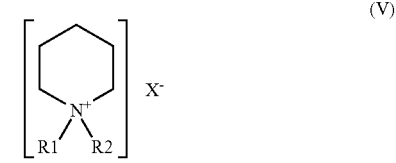
(V)

Examples of constituent cationic species of the hydrophilic ionic liquid include ammonium cations comprising 4 of the same or different substituents bound to a nitrogen atom as shown in General Formula (I), phosphonium cations comprising 4 of the same or different substituents bound to a phosphorus atom as shown in General Formula (II), imidazolium cations comprising an imdazole ring in which the two nitrogen atoms are bound to the same or different substituents as shown in General Formula (III), pyridinium cations comprising a pyridine ring in which the nitrogen atom is bound to a substituent as shown in General Formula (IV), piperidinium cations comprising a piperidine ring in which the nitrogen atom is bound to substituents as shown in General Formula (V), and sulfonium cations comprising 3 of the same or different substituents bound to a sulfur atom. Cation species having a cyclic structure may also have lower alkyls or other substituents bound to carbon atoms on the various rings.

Examples of preferred constituent cation species include imidazolium cations comprising an imdazole ring in which the two nitrogen atoms are bound to the same or different substituents, pyridinium cations comprising a pyridine ring in which the nitrogen atom is bound to a substituent, and piperidinium cations comprising a piperidine ring in which the nitrogen atom is bound to substituents. Two or more of these cyclic bodies may also be linked together to form a multicyclic body.

Straight-chain or branched alkyl, alkenyl or alkynyl groups or the like each having independently about 1 to 8 carbon atoms are preferred as the substituents in these cationic species (represented by R1 through R4 in General Formulae (I) through (V)). Examples of desirable alkyl groups include $C_{1-6}$ or more preferably $C_{1-4}$ straight-chain alkyl groups. Specific examples include methyl, ethyl, n-propyl, n-butyl, n-pentyl and n-hexyl groups. The substituents may also include alkoxy groups together with roughly $C_{1-4}$ alkyl groups (methyl, ethyl, n-propyl and n-butyl groups). The alkoxy group is preferably provided at the end of the alkyl chain as in a 2-methoxyethyl group.

Examples of desirable cationic species include N-methylimidazolium, N-ethylimidazolium, 1,3-dimethylimidazolium, 1,3-diethylimidazolium, 1-ethyl-3-methylimidazolium, 1-propyl-3-methylimidazolium, 1-butyl-3-methylimidazolium, 1-hexyl-3-methylimidazolium, 1,2,3-trimethylimidazolium and 1,2,3,4-tetramethylimidazolium. Other examples include N-propylpyridinium, N-butylpyridinium, 1,4-dimethylpyridinium, 1-butyl-4-methylpyridinium and 1-butyl-2,4-dimethylpyridinium. Trimethyl ammonium, ethyldimethyl ammonium, diethylmethyl ammonium, triethyl ammonium, tetramethyl ammonium, triethylmethyl ammonium, tetraethyl ammonium and the like can also be used.

One kind of cation can be used, or two or more can be used in combination. Imidazolium cations are preferred. Examples of these include 1-ethyl-3-methylimidazolium cations and other asymmetric imidazolium cations, and asymmetrical imidazolium cations such as 1-(2-methoxy)ethyl-3-methyl imidazolium cations and the like.

Halogen anions, carboxylate anions, sulfonate anions, phosphoric acid anions and the like can e.g. be used as constituent anionic species of the hydrophilic ionic liquid. Examples of halogen anions include chlorine anions, bromine anions, iodine anions and the like. Examples of carboxylate anions include $C_{1-18}$ monocarboxylate anions and dicarboxylate anions, such as formate anions, acetate anions, fumarate anions, oxalate anions, lactate anions and pyruvate anions. Examples of sulfonate anions include sulfonic acid anions, methanesulfonic acid anions, octane sulfonic acid anions, dodecane sulfonic acid anions and eicosane sulfonic acid anions and the like. Examples of phosphoric acid anions include phosphoric acid anions, methyl phosphoric acid monoester anions, ethyl phosphoric acid monoester anions, propyl phosphoric acid monoester anions, butyl phosphoric acid monoester anions, methyl phosphoric acid diester anions, ethyl phosphoric acid diester anions, propyl phosphoric acid diester anions, butyl phosphoric acid diester anions and the like. Of these, the various phosphoric acid anions, carboxylate anions and halogen anions are preferred.

For ionic liquid (A), examples of such ionic liquids include e.g., imidazolium caroboxylates, imidazolium chlorides and imidazolium dialkyl phosphates, and 1-ethyl-3-methyl imidazolium dialkyl phosphate, 1-ethyl-3-methyl imidazolium formate, 1-ethyl-3-methyl imidazolium acetate, 1-ethyl-2,3-dimethyl imidazolium acetate, 1-butyl-3-methyl imidazolium acetate, 1-ethyl-3-methyl imidazolium fumarate, 1-ethyl-3-methyl imidazolium lactate, 1-butyl-3-methyl imidazolium chloride and 1-ethyl-3-methyl imidazolium chloride are preferred. Especially desirable are 1-ethyl-3-methyl imidazolium dialkyl (especially diethyl) phosphate, 1-ethyl-3-methyl imidazolium formate, 1-ethyl-3-methyl imidazolium acetate, 1-butyl-3-methyl imidazolium acetate, 1-ethyl-3-methyl imidazolium chloride and 1-butyl-3-methyl imidazolium chloride.

The ionic liquid is a combination of cations and anions, and conventionally known cations and anions including the aforementioned cations and anions can be combined appropriately. The ionic liquid may be obtained commercially, or may be synthesized by well-known methods. The synthesis method is not particularly limited, and the cations can be synthesized as salts with chlorides, purified, and then reacted with salts of the anions for the desired ionic liquid, or else can be first produced as hydroxides and then neutralized with acids containing the anions. One kind of ionic liquid can be used or two or more can be used in combination.

The ionic liquid should preferably be as pure as possible. Impurities in the ionic liquid synthesis step can greatly affect the pH of a medium obtained by mixing the ionic liquid with a hydrophilic solvent, which in turn greatly affects the catalytic activity of the enzyme, the survival rate of the cellulase-producing microorganism and the like.

There are no particular limitations on the method of bringing the cellulose-containing material into contact with the ionic liquid. It is sufficient that the ionic liquid permeates the cellulose-containing material, and the cellulose-containing material does not necessarily have to be immersed in, dispersed in or suspended in the ionic liquid. For example, the cellulose-containing material can be permeated with the ionic liquid by supplying the cellulose-containing material so as to immerse it in a liquid phase of a sufficient quantity of the ionic liquid, or a quantity of the ionic liquid sufficient to permeate the cellulose-containing material can be supplied by spraying or the like to the cellulose-containing material so as to permeate the cellulose-containing material with the ionic liquid.

The treatment for causing the ionic liquid to permeate the cellulose-containing material can be established as necessary. One example is heating within the range of about 150° C. or less as necessary. Heating to at least 40° C., or more preferably at least 50° C., or still more preferably at least 60° C., or ideally at least 80° C. is preferred. Heating serves to promote permeation of the cellulose-containing material by the ionic liquid. Above 150° C., undesirable reactions can occur depending on the type of cellulose-containing material, while below 40° C., heating is unlikely to have any effect. The heating time is determined appropriately depending on the size (e.g. average particle size if pulverized, or average length in the case of chips) and origin (soft biomass, hard biomass, and classification within these types) of the cellulose-containing material used, as well as on whether the cellulose is dissolved in the ionic liquid or retained as a solid phase (that is, the range of structural relaxation or reduction in crystallinity of the cellulose). For example, when the cellulose is to be dissolved, the heating time can be 2 hours or more depending on the type of ionic liquid and the processing time. If structural relaxation or reduced crystallinity of the cellulose is desired, less than 2 hours is appropriate.

In the permeation step, the cellulose-containing material and ionic liquid can be mixed (agitated), or pressed, or pulverized, or ultrasound treated in order to promote permeation of the cellulose-containing material by the ionic liquid. Any of these processes including heating can be adopted independently of one another, or may be combined as appropriate. The type of treatment can be varied as necessary depending on the amounts of cellulose-containing material and ionic liquid that are used.

In order to minimize the amount of ionic liquid as much as possible, the amount of ionic liquid necessary for permeation can be supplied to the cellulose-containing material, or, as discussed, the cellulose-containing material can first be immersed in a sufficient amount of ionic liquid, and then separated from the ionic liquid by a solid-liquid separation means such as filtration or centrifugation.

It is thought that by means of such a permeation step, at least the cellulose-containing matrix of the cellulose-containing material is relaxed as the ionic liquid permeates the cellulose-containing material. It is thought that because the cellulose-containing material has been structurally relaxed by the ionic liquid, the hydrophilic regions of the cellulose are more easily exposed to solvent containing cellulase upon contact with the medium in the subsequent fermentation step, and are decomposed by the cellulase. Relaxation by the ionic liquid probably also facilitates exposure of the hydrophobic regions of the cellulose, which are then decomposed by the cellulase. When the cellulose is dissolved in the ionic liquid (particularly a hydrophilic ionic liquid), it is in a state that makes it more vulnerable to attack by the cellulase in the medium in the subsequent fermentation step. The cellulose in a cellulase-containing material that has been permeated within ionic liquid in such a permeation step can then be decomposed with cellulase.

(Solid-Liquid Separation Step)

The production method disclosed in the present specification can also include a step of solid-liquid separation in which a cellulose-containing fraction is separated from a non-cellulose-containing fraction. That is, when the purpose of the permeation step is to relax the structure of the cellulose in the cellulose-containing material rather than to dissolve the cellulose in the ionic liquid, most of the cellulose remains in the cellulose-containing material, which is a solid phase. That is, the solid phase is the cellulose-containing fraction, and the ionic liquid is the non-cellulose-containing fraction. In this case, solid-liquid separation serves not only for easily collecting the ionic liquid used in the permeation step in a form that is convenient for reuse, but also to remove excessive ionic liquid from the cellulose-containing material so that the negative effects of the ionic liquid on the cellulase and cellulase-producing microorganism can be avoided or controlled in the subsequent fermentation step, and the cellulose decomposition efficiency and fermentation efficiency can be improved. When only an amount of ionic liquid capable of permeating the cellulose-containing material or an amount close thereto is supplied in the permeation step, a solid-liquid separation step may not be necessary. Likewise, a solid-liquid separation step may not be necessary if the cellulase-producing microorganism has enhanced resistance to the ionic liquid.

When the cellulose is to be dissolved in the ionic liquid in the permeation step, on the other hand, the liquid phase (ionic liquid) is the cellulose-containing fraction, and the solid phase is a non-cellulose-containing fraction that contains lignin and the like as dissolved residues. Consequently, separating and collecting the ionic liquid in the solid-liquid separation step allows the fermentation step to be free of dissolved residues and other contaminants including lignin and the like.

The non-cellulose-containing fraction may be a fraction containing no cellulose at all, but may alternately contain some cellulose.

The method of solid-liquid separation in the solid-liquid separation step is not particularly limited. Examples include filtration, expression, centrifugation, separation by sedimentation and the like. Pressing or the like may also be done as necessary during filtration to achieve better separation. A cellulose-containing fraction that has been structurally relaxed at least in part by ionic liquid can also be pulverized or crushed during solid-liquid separation, as in expression or the like. When the permeation step is aimed at structurally relaxing the cellulose, the ionic liquid is separated as a liquid phase from the cellulose-containing fraction by means of the solid-liquid separation step, and the cellulose-containing material is isolated as the solid phase. It is thought that in the isolated cellulose-containing material, residual ionic liquid is retained in some form in the relaxed cellulose and the like. The residual ionic liquid in the cellulose-containing material is thought to serve a useful role in exposure of the cellulose to cellulase in the subsequent fermentation step.

(Fermentation Step)

The method for producing a useful substance disclosed in the present specification is provided with a step in which carbon sources including the cellulose in the cellulose-containing material are simultaneously saccharified and fermented by a cellulase-producing microorganism in the presence of an ionic liquid. With this fermentation step, it is possible to eliminate or simplify harsh, energy-intensive pre-treatment and washing to remove the effects of such treatment, and no separate saccharification step is needed when producing a useful substance by fermentation using a cellulose-containing material.

The fermentation step is performed in the presence of the ionic liquid used in the permeation step. The concentration of the ionic liquid in the fermentation step is preferably 500 mM or less. This is because both survivability and fermentation ability tend to be lower at concentrations over 500 mM. 300 mM or less is more preferable. This is because the effects of the ionic liquid on survivability and fermentation ability are reduced at concentrations of 300 mM or less. 200 mM or less is still more preferable. This is because at 200 mM or less, the survivability and fermentation ability are roughly equivalent to what is obtained without any addition of the ionic liquid.

The carbon sources used in the fermentation step include dissolved, disintegrated or structurally relaxed cellulose. In order to ensure proliferation of the microorganism immediately after the start of culture, the carbon sources may also include glucose and other sugars that are intrinsically available to the microorganism. Embodiments of the fermentation step are not particularly limited. As shown in FIG. 2(a), when there is a solid-liquid separation step, the cellulase-producing microorganism is supplied, together with a medium suited to its proliferation and fermentation, to the cellulose-containing fraction after solid-liquid separation to initiate the fermentation step. As shown in FIG. 2(b), when there is no solid-liquid separation step, the medium and cellulase-producing microorganism are supplied to a mixture of the cellulose-containing material and ionic liquid after the permeation step to initiate the fermentation step.

The microorganism used in the fermentation step is not particularly limited, and may be any microorganism capable of producing cellulase and decomposing cellulose. "Cellulase" is a general term for a variety of organisms that act to hydrolyze cellulose into glucose. Examples of cellulase in the narrow sense include beta-1,4-endoglucanase (EC 3.2.1.4), glucan 1,4-beta-glucosidase (EC 3.2.1.74), cellulose 1,4-beta-cellobiosidase (EC 3.2.1.91), beta-glucosidase (EC 3.2.1.21) and the like. The cellulase may be naturally occurring or artificially modified. The naturally occurring cellulase is not particularly limited, but cellulase from *Clostridium thermocellum* and other *Clostridium* species, *Trichoderma reesei* and other *Trichoderma* species and *Aspergillus oryzae, Aspergillus niger* and other *Aspergillus* species can be used by preference. Cellulase derived from Pyrococcus and other archaeal hyperthermophiles can also be used.

In the present invention, one such cellulase in the narrow sense can be used, or two or more may be used in combination. When two or more kinds of cellulases are combined, they may be of the same or different species. Cellulases of different origins can also be combined. The cellulase produced by a microorganism must be in a form that permits the cellulase-producing microorganism to use cellulose, but is preferably combined in such a way that the cellulose can be decomposed into glucose.

A microorganism capable of producing one or two or more types of cellulases required by the microorganism itself for using cellulose, or one that has been genetically modified to produce the necessary cellulase, is selected as the cellulase-producing microorganism. Two or more microorganisms can be used in combination in the same fermentation step.

Microorganisms that can be used include yeasts as well as *E. coli, B. subtilis, Aspergillus oryzae* and other microorganisms that are capable of using glucose to produce useful substances, and for which recombinant strains have been established. The microorganism may be one that has had one or two or more enzymes substituted or added by recombination to the glucose metabolism, thereby allowing it to produce a compound that is not an intrinsic metabolite.

Various known yeasts can be used without any particular limitations. Examples include *Saccharomyces cerevisiae* and other *Saccharomyces* yeasts, *Schizosaccharomyces pombe* and other *Schizosaccharomyces* yeasts, *Candida krusei, Candida shehatae* and other *Candida* yeasts, *Pichia pastoris, Pichia stipitis* and other *Pichia* yeasts, Hansenula yeasts, Trichosporon yeasts, Brettanomyces yeasts, Pachysolen yeasts, Yamadazyma yeasts, *Kluyveromyces marxianus, Kluveromyces lactic* and other *Kluveromyces* yeasts and the like. Of these, the *Saccharomyces* yeasts are preferred from the standpoint of industrial utility, and *Saccharomyces cerevisiae* is especially desirable.

A yeast that has been modified by genetic engineering to produce a compound suitable as an industrial raw material, such as a $C_3$-$C_5$ alcohol or organic acid such as lactic acid, can also be used as the yeast. With such a yeast, a useful substance can be produced directly using cellulose as the raw material. For example, lactic acid-producing yeasts and other transformed yeasts are disclosed in Japanese Patent Application Publication Nos. 2003-334092, 2004-187643, 2005-137306, 2006-6271, 2006-20602, 2006-42719, 2006-75133 and 2006-296377, and these transformed yeasts can be used in the present invention. All contents described in these publications are incorporated by reference in part of the present specification.

The cellulase is preferably secreted or surface displayed outside the cell body of the microorganism. To cause a cellulase to be secreted outside a yeast or other cell body, the yeast can be made to produce cellulase with a known secretory signal peptide attached thereto. The cellulase can also be retained in various ways on the cell surface of the yeast or the like. One way is for the cellulase to be retained as is on the surface of the yeast cell by means of a known yeast cell surface display system. Two or more kinds of cellulase may be retained on the cell surface of the same yeast, or may be displayed on the cell surfaces of different yeasts.

When a cellulase is displayed on the cell surface of a yeast, it is desirable that the cellulase have a cell surface binding domain necessary for cell surface display. The yeast surface display system may use e.g. the surface protein alpha-agglutinin or its receptor. A peptide consisting of 320 amino acid residues from the C-terminus of the agglutinating protein alpha-agglutinin in addition to a secretion signal is used. Polypeptides and methods for displaying the desired protein on the cell surface are disclosed in WO 01/79483, Japanese Patent Application Publication No. 2003-235579, WO 2002/042483 (pamphlet), WO 2003/016525 (pamphlet), Japanese Patent Application Publication No. 2006-136223, the publications of Fujita et al. (Fujita et al., 2004, Appl. Environ. Microbial. 70:1207-1212 and Fujita et al., 2002, Appl. Environ. Microbial. 68:5136-5141), and Murai et al., 1998, Appl. Environ. Microbial. 64:4857-4861. For example, the signal sequence may be an element that is incorporated into a vector, or may form part of the cellulase gene. For protein cell surface display systems using agglutinin, a yeast display kit containing a pYD1 vector and EBY 100 *Saccharomyces cerevisiae* can be obtained from Invitrogen Co. Systems using SAG1, FL01 to FL011 and other cell surface proteins and the like can also be used as cell surface display systems. The methods described in Japanese Patent Application Publication No. 2008-263975 can also be adopted.

Another way of retaining cellulase on the surface of the yeast cell is via a protein derived from a cellulosomal scaffolding protein. The methods disclosed in Japanese Patent Application Publication Nos. 2009-33993 and 2009-142260 can be adopted with regard to cell surface display using cellulosomes. That is, a protein derived from a cellulosomal scaffolding protein can be used as a skeletal protein for retaining the cellulase on the cell surface of the yeast. Cellulosomes are formed extracellularly by anaerobic bacteria and fungi, and are normally either bound to microbial surfaces or present in culture liquid. The protein can be used for retaining cellulase whether the cellulosome is a cellulosome produced by a known anaerobic or other cellulosome-producing microorganism, or a cellulosome that will be discovered in the future, or a modification of one of these. From the standpoint of cellulose decomposition ability it is possible to use a cellulosome or a modification of a cellulosome produced by an anaerobic thermophile such as *Clostridium thermocellum* or another *Clostridium* species such as *Clostridium cellulolyticum*.

To retain the cellulase on this skeletal protein for retaining cellulase, the cellulase can be produced and secreted outside the cell by the yeast, and supplied to a first skeletal protein to be retained. Secretory production of the protein in the yeast can be accomplished e.g. by attaching a signal peptide that functions in the yeast. Examples of signal peptide sequences derived from yeasts include yeast invertase leaders, alpha factor leaders, and *Rhizopus oryzae* and *C. albicans* glucoamylase leaders. Cellulase produced extracellularly can also be brought into contact with a yeast having a skeletal protein for retaining purposes expressed on the cell surface to thereby retain the cellulase on the skeletal protein for retaining purposes.

A cellulase-producing microorganism can be obtained by causing secretory expression or cell surface display of cellulase. Genes coding for various forms of cellulase can be obtained, and the cellulase can be expressed and retained on a microorganism. Genes coding for cellulase can be obtained based on cellulase nucleotide sequences and the like obtained from databases. That is, they can be obtained as nucleic acid fragments by PCR amplification or hybridization using as the template nucleic acids from various cDNA libraries or genome DNA libraries or DNA extracted from a specific yeast. Alternatively, a cellulase gene can be synthesized as a nucleic acid fragment by various nucleic acid sequence synthesis methods known in the field, such as chemical synthesis methods and the like.

The everyday operations necessary for preparing recombinant vectors for genetic modification of microorganisms and for handling yeasts and the like as recombinant hosts are ordinary matters among those skilled in the art, and can be performed by a person skilled in the art e.g. with reference to the experimental manual of T. Maniatis and J. Sambrook (Molecular Cloning, A Laboratory Manual, Cold Spring Harbor Laboratory, 1982, 1989, 2001). The various operations for expressing exogenous proteins by such gene introduction into yeasts and various other cells can be performed e.g. in accordance with the protocols of Molecular Cloning, A Laboratory Manual, Second Edition (Maniatis et al., Cold Spring Harbor Laboratory press, 1989). Methods of vector introduction include various conventional known methods such as the calcium phosphate method, transformation, transfection, conjugation, the protoplast method, electroporation, lipofection, the lithium acetate method and other methods. Such methods are described in the manuals listed above. A yeast expressing the necessary protein can be obtained from yeasts and the like with introduced vectors by selection with a marker gene or selection by active expression.

The fermentation step can be accomplished according to the type of microorganism used and the useful substance to be produced. A static culture, shaking culture or aerated stirred culture or the like can be used as the culture for fermentation. The aeration conditions can be set appropriately as anaerobic conditions, microaerobic conditions or aerobic conditions. The culture temperature is not particularly limited, and can be in the range of 25° C. to 55° C. The culture time can be set as necessary, and can be a few hours to about 150 hours. The pH can be adjusted with an inorganic or organic acid, alkali solution, or the like. An antibiotic such as ampicillin or tetracycline can be added to the medium as necessary during culture.

By means of the fermentation step, a useful substance is produced according to the useful substance production ability of the microorganism used. For example, ethanol is obtained with ordinary yeasts, which ferment ethanol. Yeasts that have the ability to produce lactic acid and other organic acids due to biogenetic modification or the like can be used to produce lactic acid and the like. After completion of the useful substance production step, there can be a step in which the fraction containing the useful substance is collected from the culture liquid, and another step in which it is purified or concentrated. The collection process and purification or other process can be selected appropriately according to the type of useful substance and the like.

(Fermentation Residue Collection Step)

After the fermentation step, any solid-phase residue in the fermentation liquid can be collected by solid-liquid separation. The collected solid phase is the residue of decomposition by the cellulase, and the non-cellulose-fraction of the cellulose-containing material (typically containing lignin and hemicellulose) can be collected in this way. This residue can be used for various purposes because it contains a high percentage of the aromatic polymer lignin, and because this lignin has been saved from excess condensation or the like. Phenolic compounds can also be obtained by bringing this lignin into contact with lignin-decomposing enzymes. When this solid-phase residue contains residual cellulose, it can be subjected to further permeation and fermentation.

(Ionic Liquid Reuse Step)

The method for producing a useful substance disclosed in the present specification may include an ionic liquid reuse step in which the ionic liquid that has been separated from the cellulose-containing material in the solid-liquid separation step is collected and used in a further permeation step, or for some other use. The overall processing costs can be greatly reduced by reusing the ionic liquid. Ionic liquid can also be collected from the culture liquid after the fermentation step and reused. Further, ionic liquid can be collected from the culture liquid by distillation or the like.

Next, typical embodiments of the method for producing a useful substance disclosed in the present specification are explained as shown in FIG. 2. FIG. 2(a) shows one example of an embodiment in which the permeation step is aimed at structurally relaxing rather than dissolving the cellulose. In this embodiment, the structure of the cellulose in actual biomass is heated with ionic liquid and relaxed in the permeation step. The cellulose-containing material is immersed in ionic liquid and heated while in a compartment having a liquid passage part that allows passage of the ionic liquid (typically, a container at least the bottom of which is a mesh or other liquid passage part). Next, the cellulose-containing fraction is removed from the ionic liquid tank together with the compartment containing the solid phase, and immersed together with the compartment in medium containing a cellulase-producing microorganism to perform the fermentation step. After fermentation, the useful substance accumulates in the medium, while the fermentation residue (typically lignin) remains in the compartment. In this embodiment, the permeation step, solid-liquid separation step and fermentation step can be performed easily without any actual transport or the like of the ionic liquid. The ionic liquid can be reused effectively, and it is easy to collect the fermentation residue.

FIG. 2(b) shows one example of an embodiment in which the permeation step is aimed at dissolving the cellulose. In this embodiment, the cellulose in actual biomass is heated and dissolved with ionic liquid in the permeation step. The cellulose-containing material is immersed in ionic liquid and heated. The cellulose is dissolved in the ionic liquid, which is the liquid phase. Medium is added together with a cellulase-producing microorganism to the ionic liquid tank after the permeation step to perform the fermentation step. After fermentation, the useful substance accumulates in the medium, and the fermentation residue remains in the medium. In this embodiment as well, the permeation step, solid-liquid separation step and fermentation step can be performed more easily without any actual transport or the like of the ionic liquid or cellulose-containing fraction.

As explained above, because with the method for producing a useful substance disclosed in the present specification a cellulose-containing material can be converted to a useful substance and used with more simple steps than in the past, the utility (cost) of cellulose-containing material is greatly improved.

EXAMPLES

The present invention is explained in detail below using examples, but the present invention is not limited by these examples.

Example 1

Effects of Ionic Liquid on Ethanol Fermentation and Survivability by Yeast

The effects of ionic liquid on ethanol fermentation and viability of yeasts were investigated in the context of alcohol manufacture from biomass treated with ionic liquid. That is, genetically recombinant yeasts for use in simultaneous saccharification and fermentation were cultured. Yeast was transplanted from a MT 8-1 colony on YPD plate medium to YPD liquid medium (30 ml), and cultured for 24 hours at 30° C., 150 rpm. This culture liquid was added to 400 ml of YPD liquid medium to OD=0.05, and cultured for 72 hours at 30° C., 150 rpm. The cell bodies were collected by centrifugation, and washed twice with deionized water.

Ethanol fermentation was investigated with glucose as the substrate. 1-ethyl-3-methylimidazolium diethylphosphate (hereinbelow called [Emim][DEP]), 1-ethyl-3-methylimidazolium chloride (hereinbelow, [Emim][Cl]) and 1-ethyl-3-methylimidazolium acetate (hereinbelow [Emim][OAc]) were used as ionic liquids. The structural formula of each is as follows.

[C2]

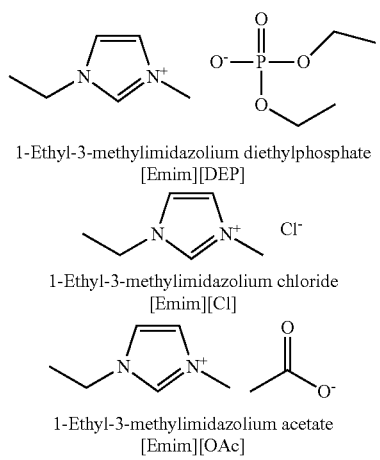

1-Ethyl-3-methylimidazolium diethylphosphate
[Emim][DEP]

1-Ethyl-3-methylimidazolium chloride
[Emim][Cl]

1-Ethyl-3-methylimidazolium acetate
[Emim][OAc]

The three ionic liquids described above were each added to YPD medium (glucose 40 g/l) containing 50 mM sodium acetate buffer (pH 5) to final concentrations of 0, 50, 100, 200, 500 and 1000 mM. Yeast was added to these solutions to a concentration of OD=20, the final volume was adjusted to 2 ml, and fermentation was initiated at 30° C., 200 rpm in test tubes capped with silicon plugs penetrated by syringe needles. Fermentation was also performed in a system without ionic liquid as a control test.

100 μl samples were taken from the fermentation liquid at fixed intervals (4 hours, 6 hours, 24 hours), and the yeast was removed by centrifugation. 20 μl of supernatant was diluted to 200 μl with ionized water, and 900 μl of acetone and 50 μl of 1-propanol as the internal standard substance were added to 50 μl of this diluted sample. Resulting waste was removed by centrifugation, and the ethanol concentration of the supernatant was measured by gas chromatography.

Figure 3:
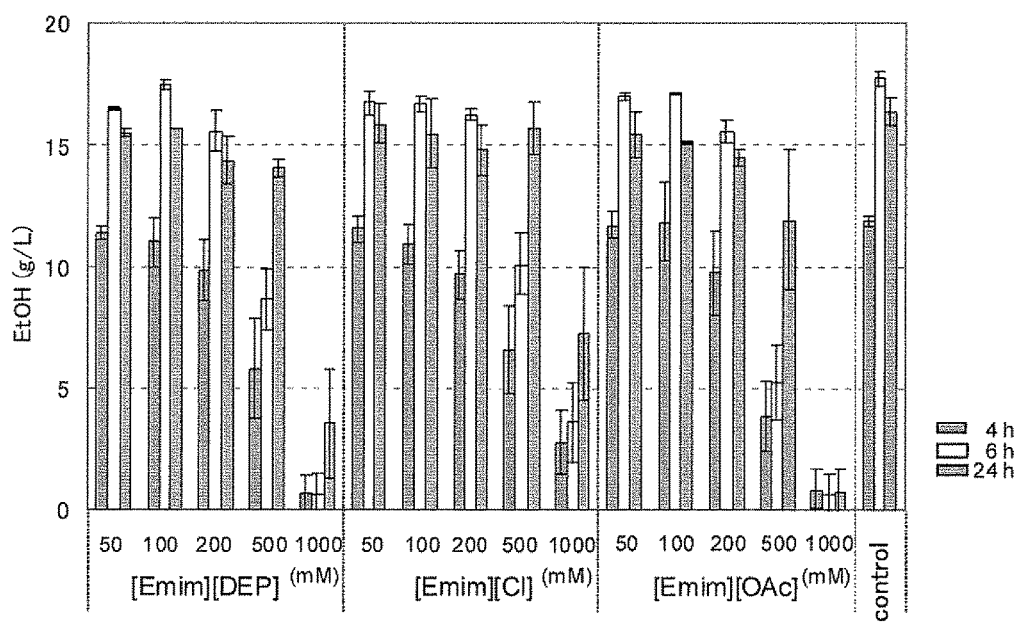
FIG. 3 shows the ethanol fermentation behavior of yeast in the presence of various ionic liquids.

The ethanol fermentation behavior of the yeast in the presence of each ionic liquid is shown in FIG. 3. Regardless of which ionic liquid was added, fermentation behavior was similar to that of the control up to an ionic liquid concentration of about 200 mM, and adequate ethanol fermentation was seen. At an ionic liquid concentration of 500 mM, ethanol productivity declined, and fermentation ability was much lower at 1000 mM. The type of ionic liquid did not appear to have any great effect on fermentation ability.

Figure 4:
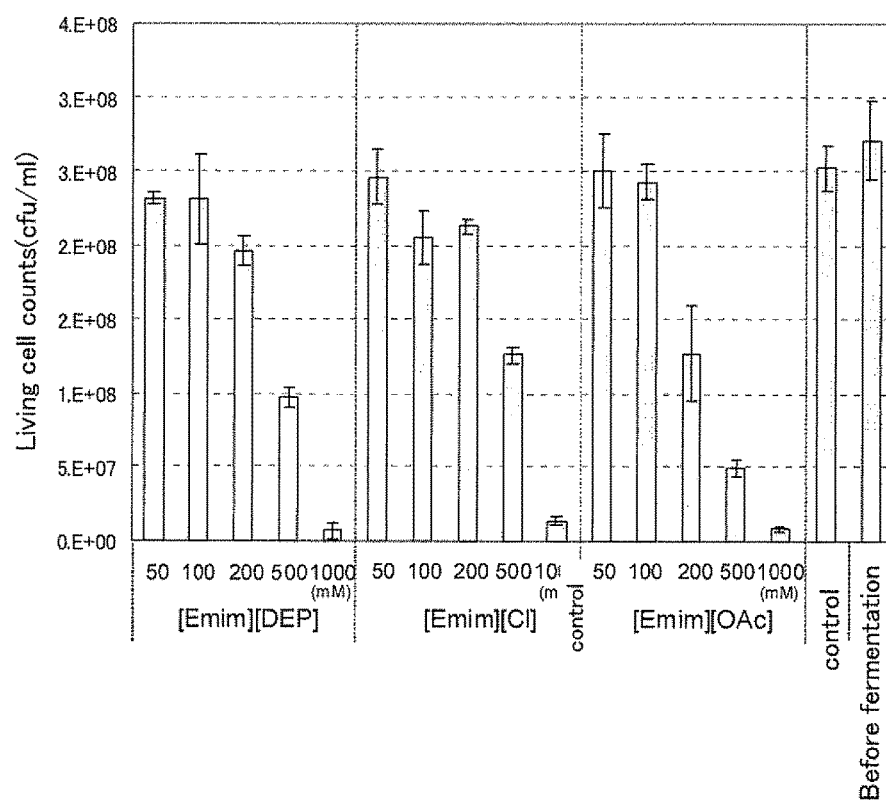
FIG. 4 shows surviving cell counts of yeasts in fermentation medium in the presence of various concentrations of ionic liquids.

Live cell counts of yeasts in fermentation medium containing various concentrations of ionic liquid are shown in FIG. 4. Using [Emim][DEP] and [Emim][Cl], yeast survivability was not greatly affected up to an ionic liquid concentration of 200 mM. These results confirm that yeasts survive and fermentation progresses in mixed solutions of ionic liquid.

Example 2

One-Step Alcohol Fermentation from Ionic Liquid-Treated Cellulose

In this example, the following experiment was performed using recombinant yeast (arming yeast) displaying a cellulose-decomposing enzyme on the cell surface in order to verify the process shown in FIG. 2(b). That is, a recombinant yeast for use in simultaneous saccharification and fermentation was cultured. Yeast was transplanted from a colony of cellulase surface-displaying yeast (arming yeast) on minimum medium (SD selection) plate medium to 30 ml of SD selection liquid medium, and cultured for 24 hours at 30° C., 150 rpm. This culture liquid was added to OD=0.05 to 400 ml of SD medium with casamino acid added thereto to a final concentration of 20 g/l (SDC selection medium), and cultured for 96 hours at 30° C., 150 rpm. The cell bodies were collected by centrifugation, and washed twice with deionized water.

This cellulase surface-displaying yeast (arming yeast) is a recombinant yeast in which cellobiohydrase, endoglucanase and beta-glucosidase are expressed by cell surface display. Details about this yeast are disclosed in Appl. Environ. Microbiol. (2004) 70:1207-1212: Synergistic Saccharification, and Direct Fermentation to Ethanol, of Amorphous Cellulose by Use of an Engineered Yeast Strain Codisplaying Three Types of Cellulolytic Enzyme; Yasuya Fujita, Junji Ito, Mitsuyoshi Ueda, Hideki Fukuda and Akihiko Kondo.

Figure 5:
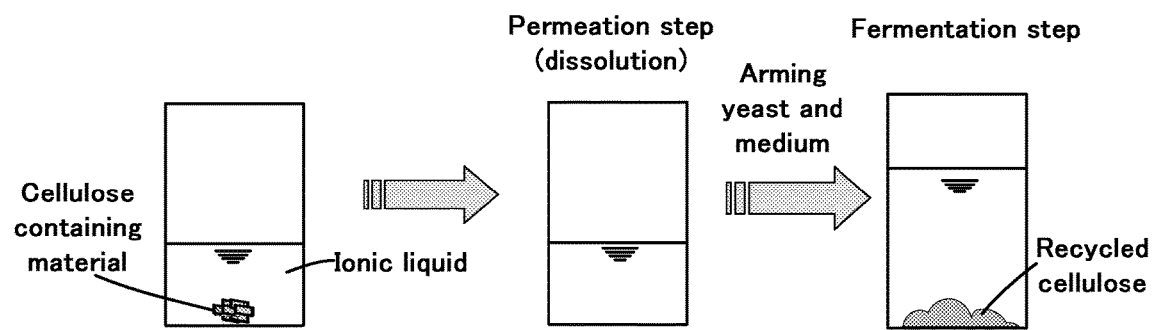
FIG. 5 shows an outline of the operations in Example 2.

Next, cellulose was pretreated with ionic liquid. 100 mg of crystalline cellulose (Avicel PH-101, Fluka) and 1.056 g of [Emim][DEP] ionic liquid were placed in a test tube (30 mm di.), which was then set in a ChemiStation (Tokyo Rika Kikai) and heated for 2 hours at 80° C. while being agitated in a cross-shaped Teflon agitator to completely dissolve the cellulose. This was cooled to room temperature, and 5 ml of 200 mM sodium acetate buffer (pH 5.0) was added and left for 1 hour to produce a lump of semi-transparent recycled cellulose with the consistency of agar. 4.09 ml of deionized water, 5 ml of 4×YP medium and arming yeast to OD=20 were added, and the final volume was adjusted to 20 ml. Fermentation was performed at 30° C., 200 rpm in a test tube topped with a silicon plug penetrated by a syringe needle. The fermentation liquid was sampled at 24-hour intervals, and the ethanol concentration was assayed by gas chromatography. The sequence of operations is shown in FIG. 5.

Figure 6:
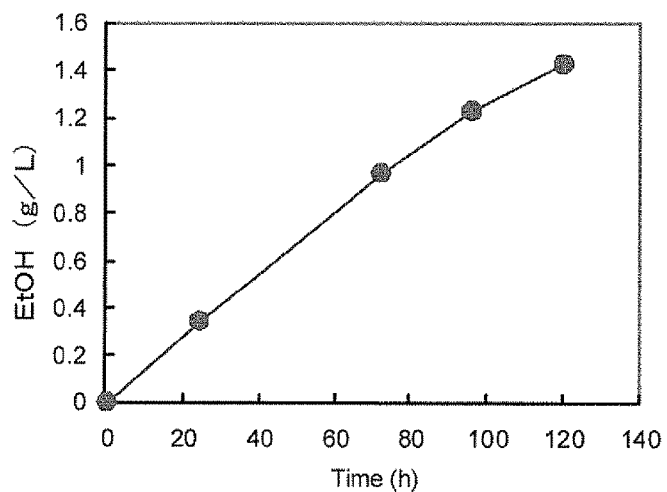
FIG. 6 shows ethanol fermentation by arming yeast (yeast displaying cellulase on the cell surface) from cellulose pretreated with ionic liquid.
Figure 7:
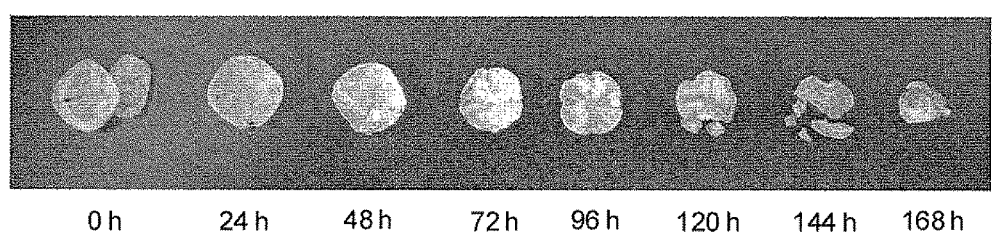
FIG. 7 shows the decomposition trend of recycled cellulose.

FIG. 6 shows the ethanol fermentation behavior of arming yeast using cellulose pretreated with ionic liquid. In medium containing [Emim][DEP], the arming yeast converted cellulose pretreated with [Emim][DEP], producing ethanol. 1.43 g/l of ethanol was obtained 120 hours after the start of fermentation, corresponding to about 56% of a theoretical yield. As shown in FIG. 7, moreover, as fermentation progressed a reduction in the amount of recycled cellulose (the carbon source) could be seen with the naked eye.

Figure 8:
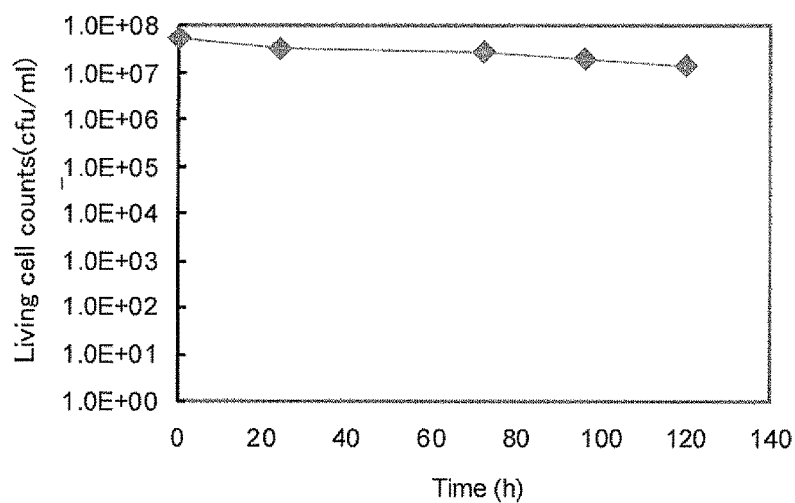
FIG. 8 shows the surviving cell counts of yeast at various times after the start of fermentation.

FIG. 8 shows live cell counts of yeast at various times after the start of fermentation. This shows that arming yeast survives and performs fermentation even in the presence of ionic liquid. These results confirm that alcohol can be obtained by adding recombinant yeast directly to a reaction solution of cellulose that has been treated with ionic liquid. Consequently, an alcohol production process such as that shown in FIG. 2(b) has been shown to be feasible.

Example 3

Alcohol Fermentation from Actual Biomass Treated with Ionic Liquid

In this example, the following experiment was performed using the recombinant yeast (arming yeast) used in Example 2 displaying a cellulose-decomposing enzyme on the cell surface in order to verify the process shown in FIG. 2(a). That is, a recombinant yeast for use in simultaneous saccharification and fermentation was cultured. Yeast was transplanted from a colony of cellulase surface-displaying yeast (arming yeast) on minimum medium (SD selection) plate medium to 5 ml of SD selection liquid medium, and cultured for 40 hours at 30° C., 120 rpm. This culture liquid was added to 50 ml of SDC selection medium, and cultured for 48 hours at 30° C., 100 rpm. The cell bodies were collected by centrifugation, and washed twice with deionized water.

Figure 9:
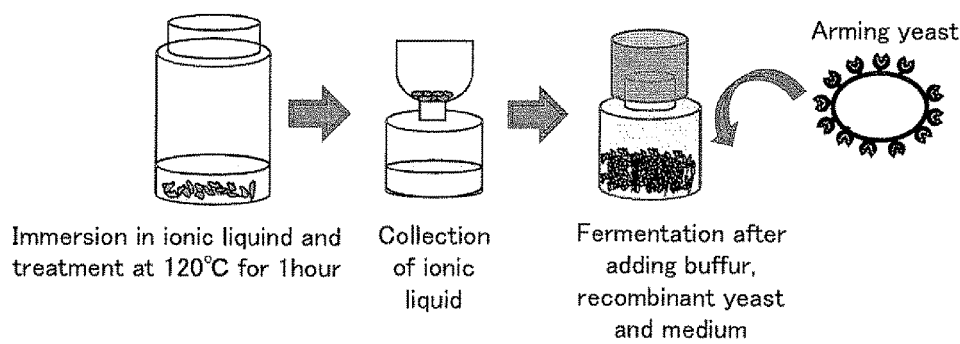
FIG. 9 shows an outline of the operations in Example 3.

Next, cellulose was pretreated with ionic liquid. 300 mg of bagasse powder pulverized to a grain size of about 4 mm and 10 g of [Emim] [OAc] ionic liquid were added to a vial, and reacted under static conditions for 30 minutes at 120° C. 10 ml of sterile water was added to the vial, the solution was separated with a filter and only the biomass sample was collected. This biomass sample was transferred to a separate container, 2.5 ml of 4×YP medium, 5.5 ml of citric acid buffer and 2 ml of the aforementioned arming yeast concentrated to OD=50 were added, and the final volume was adjusted to 10 ml. Simultaneous saccharification and fermentation was performed with the container at 30° C., 300 rpm. The fermentation liquid was sampled at 24-hour intervals, and the ethanol concentration was assayed with an enzyme sensor. FIG. 9 shows the sequence of operations, while FIG. 10 shows the ethanol fermentation behavior of the arming yeast from cellulose pretreated with ionic liquid.

Figure 10:
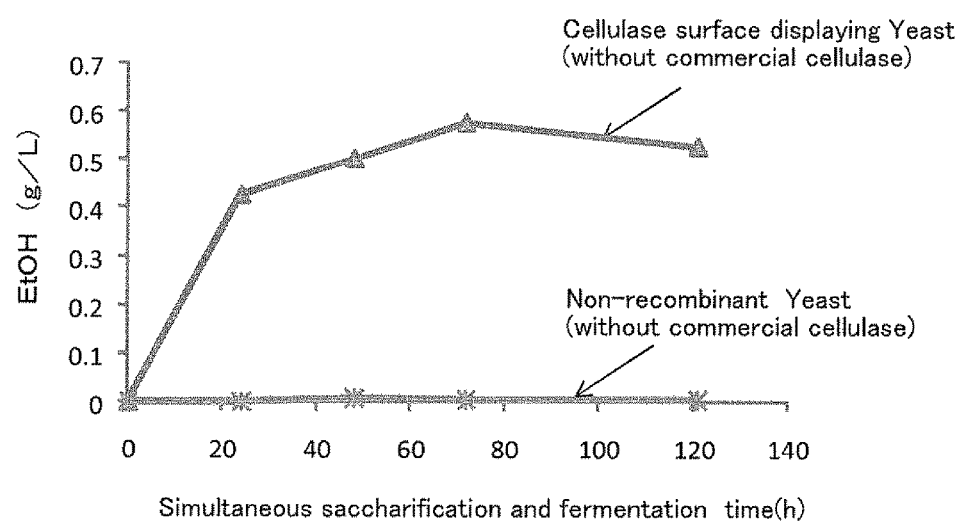
FIG. 10 shows ethanol fermentation by arming yeast (yeast displaying cellulase on the cell surface) from cellulose-containing material (bagasse) pretreated with ionic liquid.

As shown in FIG. 10, in contrast to the non-recombinant control yeast, ethanol production from actual biomass was confirmed in the sample with added arming yeast even though no commercial cellulase was added. These results show that alcohol can be produced by adding recombinant yeast directly to a reaction solution of cellulose that has been pretreated with ionic liquid. This shows that an alcohol production process such as that shown in FIG. 2(a) is feasible.

What is claimed is:

1. A method for producing a useful substance from a cellulose-containing material, comprising:
   bringing a cellulose-containing material into contact with an ionic liquid to cause the ionic liquid to permeate the cellulose-containing material; and
   simultaneously saccharifying and fermenting a carbon source in the presence of the ionic liquid that comprises the cellulose in the cellulose-containing material using a cellulase-producing microorganism to produce the useful substance, wherein a concentration of the ionic liquid ranges from 50 to 500 mM, and wherein the useful substance produced is selected from the group consisting of alcohols, organic acids, glycerin, and plastics.

2. The method according to claim 1, wherein the bringing of the cellulose-containing material into contact with the ionic liquid comprises heating the cellulose-containing material and the ionic liquid.

3. The method according to claim 1, further comprising:
   performing solid-liquid separation for separating a cellulose-containing fraction from a non-cellulose-containing fraction after bringing the cellulose-containing material into contact with the ionic liquid.

4. The method according to claim 1, wherein the ionic liquid comprises a hydrophilic ionic liquid.

5. The method according to claim 1, wherein the microorganism is a recombinant yeast expressing cellulase.

6. The method according to claim 5, wherein the recombinant yeast is a yeast that secretes or surface displays the cellulase.

7. The method according to claim 3, further comprising:
   collecting the ionic liquid that is in the non-cellulose-containing fraction that has been separated in the solid-liquid separation, and supplying the ionic liquid to the cellulose-containing material to bring the cellulose-containing material into contact with the ionic liquid.

8. The method according to claim 1, wherein the microorganism is a yeast secreting or surface displaying cellulase.

9. The method according to claim 1, wherein the cellulose-containing material is a material containing polymers and derivatives of polymers formed from glucose by polymerization with β-1,4-glucoside bonds.

10. The method according to claim 1, wherein the cellulase-producing microorganism is selected from the group consisting of *Clostridium*, *Trichoderma*, *Aspergillus*, *Escherichia coli*, *Bacillus subtilis*, yeasts, genetically modified yeasts, and combinations thereof,
    wherein the genetically modified yeast is modified to produce cellulase.

11. The method according to claim 1, wherein the substance produced is selected from ethanol, propanol, isopropanol, butanol, and isobutanol.

12. The method according to claim 1, wherein the concentration of the ionic liquid ranges from 50 to 300 mM.

13. The method according to claim 1, wherein the concentration of the ionic liquid ranges from 50 to 200 mM.

14. The method according to claim 1, wherein the cellulose-containing material comprises lignan.

15. The method according to claim 1, wherein the ionic liquid has 1-ethyl-3-methyl-imdazolium as a cationic species.

16. A method for producing a useful substance from a cellulose-containing material, comprising:
    bringing a cellulose-containing material into contact with an ionic liquid to cause the ionic liquid to permeate the cellulose-containing material; and
    simultaneously saccharifying and fermenting a carbon source in the presence of the ionic liquid that comprises the cellulose in the cellulose-containing material using a cellulase-producing microorganism to produce the useful substance,
    wherein a concentration of the ionic liquid ranges from 50 to 500 mM, wherein the useful substance produced is selected from the group consisting of alcohols, organic acids, glycerin, and plastics, and
    wherein the microorganism comprises a yeast secreting or yeast surface displaying cellulase.

17. The method according to claim 16, wherein the microorganism is a yeast surface displaying cellulase.

* * * * *